(12) United States Patent
Yokoyama et al.

(10) Patent No.: US 8,039,226 B2
(45) Date of Patent: Oct. 18, 2011

(54) ANTI NC1 MONOCLONAL ANTIBODY

(75) Inventors: Tsukao Yokoyama, Kiyose (JP); Toshiyuki Imasawa, Chiba (JP)

(73) Assignee: Tsukao Yokoyama, Kiyose-Shi (JP)

( * ) Notice: Subject to any disclaimer, the term of this patent is extended or adjusted under 35 U.S.C. 154(b) by 745 days.

(21) Appl. No.: 10/589,420

(22) PCT Filed: Feb. 15, 2005

(86) PCT No.: PCT/JP2005/002669
§ 371 (c)(1),
(2), (4) Date: Aug. 15, 2006

(87) PCT Pub. No.: WO2005/082940
PCT Pub. Date: Sep. 9, 2005

(65) Prior Publication Data
US 2007/0161048 A1    Jul. 12, 2007

(30) Foreign Application Priority Data
Feb. 16, 2004 (JP) ................................. 2004-073468

(51) Int. Cl.
| | |
|---|---|
| *G01N 33/531* | (2006.01) |
| *G01N 33/543* | (2006.01) |
| *G01N 33/544* | (2006.01) |
| *G01N 33/567* | (2006.01) |
| *G01N 33/577* | (2006.01) |
| *G01N 33/60* | (2006.01) |
| *C07K 16/18* | (2006.01) |
| *C12P 21/08* | (2006.01) |

(52) U.S. Cl. .......... 435/7.92; 435/7.1; 435/7.2; 435/7.5; 435/7.94; 435/7.95; 435/40.5; 435/40.52; 436/503; 436/504; 436/506; 436/518; 436/548; 436/63; 530/388.2; 530/388.9; 530/391.1; 530/391.3

(58) Field of Classification Search ............. 435/7.2, 435/7.92, 7.94, 7.95, 40.5, 7.1, 7.5, 40.52; 436/506, 518, 535, 547, 548, 63, 503, 504; 424/9.1, 9.34, 140.1, 141.1; 530/388.2, 388.9, 530/391.1, 391.3, 413
See application file for complete search history.

(56) References Cited

U.S. PATENT DOCUMENTS
5,656,298 A * 8/1997 Kitchell et al. .............. 424/486
5,871,649 A * 2/1999 Ofsthun et al. .............. 210/645
6,696,281 B1 * 2/2004 Chambers et al. ......... 435/235.1

OTHER PUBLICATIONS

Borza et al., 2001. The NC1 domain of collagen IV encodes a novel network composed of the alpha1, alpha2, alpha5, and alpha6 chains in smooth muscle basement membranes. J. Biol. Chem. 276: 28532-28540.*
Johansson et al., 1992. The structural organization of type IV collagen. Identification of three NC1 populations in the glomerular basement membrane. J. Biol. Chem. 267: 24533-24537.*
Campbell, 1991. Monoclonal Antibody and Immunosensor Technology, Elsevier, Amsterdam. pp. 3-6 and 45.*
Lan et al., 1997. Local macrophage proliferation in the pathogenesis of glomerular crescent formation in rat anti-glomerular basement membrane (GBM) glomerulonephritis. Clin. Exp. Immunol. 110: 233-240.*
Ninomiya, Y., et al., "Differential Expression of Two Basement Membrane Collagen Genes, COL4A6, COL4A5, Demonstrated by Immunofluorescence Staining Using Peptide-specific Monoclonal Antibodies," The Journal of Cell Biology, vol. 130, No. 5, pp. 1219-1229 Sep. 1995.
Sugihara, K. et al., "Experimental anti-GBM glomerulonephritis induced in rats by immunization with synthetic peptides based on six α chains of human type IV collagen," Journal of Pathology, vol. 178 pp. 352-358 Mar. 1996.
Yokoyama, K. et al., "Experimental glomerulonephritis induced by NC1 domain of type IV collagen (K 35)," The Cell, vol. 34, No. 4, pp. 36-39 Apr. 20, 2002.
Yokoyama, K. et al., "The assay of the NC1 (carboxyterminal domein of type IV collagen) & AntiNC1 antibody contained in urine and serum," The Cell, vol. 35, No. 4, pp. 40-44 Apr. 20, 2003.
Correspondence sent by Collagen Research Center (Tokyo, Japan) to Cosmo Bio Co Ltd. (Tokyo, Japan), (2002).
A product listing of Cosmo Bio Co Ltd. (Tokyo, Japan) (2003).
A catalog of Cosmo Bio Co Ltd. For 2003 to 2005 (Tokyo Japan), 3 pages, (2003).

* cited by examiner

*Primary Examiner* — Mark Shibuya
*Assistant Examiner* — James L Grun
(74) *Attorney, Agent, or Firm* — Knobbe, Martens, Olson & Bear, LLP (57) ABSTRACT

The present invention dedicates to detect nephritis in early stage of either primary or secondary nephritis using an anti NC1 monoclonal antibody. The present invention dedicates to provide useful information for diagnosis of renal function to detect NC1 by immunofluorescent stain method in renal biopsy section obtained at early stage where immunoglobulins do not deposit yet in renal GBM etc, or by antigen-antibody reaction in urine or serum specimens. Furthermore, the present invention comprises to utilize for therapeutic use.

11 Claims, 6 Drawing Sheets
(6 of 6 Drawing Sheet(s) Filed in Color)

Control

Anti-GBM nephritis(No.2301)

Fig.3-1.

Control

Anti-GBM nephritis(No.2301)

Fig.3-2

Control

Anti-GBM nephritis(No.2301)

Fig. 4
1. IgA nephropathy

2. Diabetic nephropathy

3. Minimal change type nephrosis

4. Minimal change type nephrosis (after treatment)

5. Normal kidney

ANTI NC1 MONOCLONAL ANTIBODY

This application is the U.S. National Phase under 35 U.S.C. §371 of International Application PCT/JP2005/002669, filed Feb. 15, 2005, which claims priority to Japanese Patent Application No. 2004-073468, filed Feb. 16, 2004. The International Application was not published under PCT Article 21(2) in English.

TECHNICAL FIELD

The present invention relates to a method and reagent of detecting nephritis using anti NC1 monoclonal antibody. Furthermore, therapeutic implements and medicines are embraced therein.

BACKGROUND ART

Main conventional parameters to detect or diagnose nephritis using the urine sample include the presence and/or level of a protein, albumin, type IV collagen (three chains-domain) and β 2M etc. Further, conventional definite diagnostic method for nephritis depends on a method of staining renal slice samples obtained by renal biopsy in order to observe the deposit of immunoglobulin (hereafter referred to as Ig) or formation of crescents. For example, in order to diagnose IgA nephropathy, detecting "granular deposit of IgA mainly in diffused mesangial region of kidney" may need to be done, for example, as described in p. 1071 of Laboratory Examination (2001~2002; published by BUNKO-DO). The foregoing detecting granular deposit of IgA can be done by an immunofluorescence assay or enzyme immunoassay, however, it may necessarily require the renal biopsy procedures.

DISCLOSURE OF INVENTION

Problems to be Solved by the Invention

These foregoing methods, however, include the following problems:

The definite diagnosis may need high diagnostic techniques of well experienced pathologists. In addition, at the time when the deposit of Igs is detected, the stage of the nephritis might have already progressed for a long period, sometime for several decades and its renal function might have remarkably decreased. Therefore, in order to diagnose nephritis more simply and more precisely, a better diagnostic method that can diagnose a kidney disease at a very early stage even before deposit of Ig and/or formation of glomerular crescent can be observed has been aspired

Means for Settlement of the Problems

The present invention can diminish some problems as mentioned above and dedicates detection methods and detecting reagents for diagnosing nephritis in its early stage and further dedicates a sero-cleaning method.

The present inventors, heretofore, have suggested that a common antibody detected from various types of nephritis is specific to NC1 domain of type IV collagen. In fact, the present inventors have detected anti NC1 antibody with high frequency from the serum or urine in various types of nephritis including anti glomerular basement membrane (GBM) antibody nephritis. It has been reported that the antigen of the antibodies detected from the anti GBM antibody nephritis is a part of NC1 domain. There is no antibody prepared artificially that can bind the antigen only at the crisis. Furthermore, existence of a common antibody in various types of nephritis cannot have been detected by an immunohistofluorescent staining method. Thereupon, the present inventors prepared an anti NC1 monoclonal antibody by sensitizing the antigen NC1 isolated and purified from bovine renal glomeruli with the mouse and accomplished "Anti NC1 monoclonal antibody" and "Labeled anti NC1 monoclonal antibody". In some embodiments, such antibodies can be applicable to the Western blot method or immunofluorescent staining method, and further to a "NC1 detecting ELISA kit with sandwich technique".

The procedures are as follows:
1. [Isolation and purification of antigen] Isolate type IV collagen NC1 domain (hereinafter referred as NC1) from the raw material of bovine renal glomeruli and purify it by column chromatography (J. Biol. Chem., 263, 10481-8).
2. [Preparation and selection of anti NC1 monoclonal antibody] Prepare monoclonal antibody using the mouse by the usual method (Monoclonal Antibody Experimental Manual, published by KODAN-Sha, 1987).

For screening of the cell fusion, select a lot of positive pores showing high antibody titer from an ELISA assay and further select the antibody responding to a NC1 monomer and/or NC1 dimmer by Western blot techniques. Then, perform an immunofluorescent staining and firstly select an antibody that can stain the sample from the monkey anti glomerular basement membrane (GBM) antibody nephritis but not the sample from the normal monkey kidney. The resulting anti NC1 monoclonal antibody can be applicable to not only ELISA method, Western blot method but also immunofluorescent stain method.

Of course, such anti NC1 monoclonal antibody is preferred to be applied to only one method or two or more methods among ELISA, Western blot, immunofluorescent stain or other methods. Such anti NC1 monoclonal antibody, however, is most preferable to be applied to any method. In some immunofluorescent stain methods, antibodies responding to a normal kidney and polyclonal antibodies prepared from the rabbit etc. are acceptable and useful to detect existence of the tissues. However, those antibodies may not be used to discriminate between nephritis and normal kidney.

A crab-eating macaque nephritis model can be established by dorsal injection of 1 mg of initial dose and 3 mg of booster dose of NC1 which is different from the previous reports using plantar injection. The merits of dorsal injection include no difficulties in walking and less infection in the animal. More specifically, in the dorsal injection, it is preferable to inject the larger booster dose compared to the initial dose rather than 4 mg of single dose or smaller or equivalent booster dose compared to the initial dose. Further specifically, more than 1.5-fold booster dose is more preferable and 3-fold is most preferable compared to the initial dose.

This theory is usefully applicable to prepare type II collagen arthritis model etc. in sensitized animal or to provide various vaccinations. For example, in the case of vaccination of hepatitis type B, the conventional booster dose, sometime, may not increase its antibody titer. In such case, more than 1.5-fold booster dose higher than the conventional single dose or ½ initial dose is preferred. Also 3-fold higher in booster dose than the conventional initial dose is more preferable.

"Anti NC1 monoclonal antibody" of the present invention stains the renal glomerular basement membrane (GBM) of the pathological sections obtained from monkey GBM antibody nephritis or human IgA nephropathy using an indirect immunofluorescent stain method. Furthermore, this antibody stains similarly other pathological sections obtained from other animal species such as the rat and mouse etc. or other various kinds of human nephritis other than the IgA nephropathy. "NC1 assay ELISA kit" of the present invention is useful for the early detection of primary nephritis and secondary nephritis such as diabetic nephritis etc. More specifically, in "Anti GBM antibody nephritis", the anti NC1 monoclonal antibody reacts significantly with NC1 which is abundant in GBM at injury crisis. Therefore, it can obtain particularly good hypersensitivity and provide sensitive detection of NC1 in urine as well as in serum samples.

Furthermore, anti NC1 antibody in serum or urine of a HIGA mouse IgA nephropathy model can be detected by an ELISA method with an "Anti NC1 monoclonal antibody" as the positive standard. In any case of glomerular nephritis such as some types of nephritis, diabetes, hypertension models etc., an assay or detection of anti NC1 antibody may be a significant indicator of the disease progression. In the other cases of nephritis occurred from infection or other disease models, an assay or detection of anti NC1 antibody may also be a good indicator of the disease progression.

The present inventors established the following operative means for "NC1 assay ELISA kit" in order to detect nephritis in an early stage. More specifically, the detecting method and the assay reagents in order to detect NC1 using the urine sample obtained from anti GBM antibody nephritis patient as well as using the serum sample will be exemplified and detailed below. However, the present invention should not be construed as being limited thereto.

1. NC1 Detecting Method and Assay Reagents in Serum and/or Urine.

NC1 can be detected using the following reagents: 1) an Anti NC1 antibody (derived from rabbit)-coated plate, 2) an Enzyme (HRP)-labeled anti NC1 monoclonal antibody, 3) a Coloring substrate (TMB), 4) a Reaction stopper solution (sulfuric acid).

Hereupon, it is preferable to prepare non-labeled "2)" and add "Enzyme (HRP) labeled anti mouse IgG antibody" as "2)-2". Further, it is preferable to exchange their antibody parts between "1)" and "2)" or to change the both into monoclonal antibody.

Hereunto, the positive standard is preferably obtained from the human patient but more preferably obtained from the monkey of an experimental model invented by the present inventors. It is because the more stable standard can be obtained from the monkey which is more carefully bred and well-controlled. More specifically, it is preferable to make the human patient sample to a primary standard and the sample derived from the monkey to a secondary standard that can be equipped in the assay kit.

Immune reaction assay methods include not only an enzyme immunoassay method which is representatively used but also an AB method, RIA method, immunoluminescence method, precipitation method, agglutination method etc. An enzyme labeled antibody in the enzyme immunoassay includes the both antibodies without distinction as to a polyclonal or monoclonal antibody. Furthermore, the antibody can be preferably equipped into a radio-labeled compound (RIA method), lumino-labeled compound (immunofluorescence method) or non-labeled compound (precipitation method, agglutination method).

The reaction mode includes not only a sandwich method but also a competitive method etc. The sandwich method is, however, specifically more preferable. For a composition of assay reagents, an anti NC1 antibody coated plate can preferably be made of a glass or magnetic substance, or a method without solid phase method that does not use plate is also preferably accepted.

When anti NC1 antibody (hereinafter referred to as the antibody) is coated on a plate, such a coating substance can preferably be indirectly coated on a plate and the coating substance may include adipic acid, biotin, or combined substance of them.

An antigen can preferably be prepared from bioextracts, recombinants, or constructive peptides (including specified fractions or synthesized materials). Then the antibody can preferably be prepared from these antigens.

The animal species of antigens using for the assay reagents include preferably not only a human but also a monkey, bovine, swine, chicken, sheep, goat, rabbit, rat etc, but not limited to them. Further, the antigen can preferably include mixed antigens from multi-animal species.

The antigen-derived organ includes preferably the kidney, but not limited to it.

2. Anti NC1 Antibody Remover and/or NC1 Remover.

NC1 in sera can only be removed by dialysis of the blood through an affinity column prepared with the anti NC1 antibody. The anti NC1 antibody in sera can only be removed by dialysis of the blood through an affinity column prepared with NC1. After these treatments, the blood from which both antibody and antigen are removed will be recycled into the internal circulation of the body. Application of this principle to the crab-eating macaque nephritis model {sensitized by [K35 NC1] (provided by Collagen Research Center)} showed that the concentrations of both antigen and antibody in urine become less than half after treatment. In conventional dialysis, however, the concentrations of both the antigen and antibody in the patient serum may not show such differences after treatments as mentioned above. Of course, any remover of NC1 and/or anti NC1 antibody in serum may preferably be included, but not limited to the above mentioned removers. Further, it is preferable to replace NC1 or anti NC1 antibody with α 3-chain group, α 4-chain group and/or their antibodies. It is also preferable to replace them with α 3-chain antigen part, α 4-chain antigen part inducing anti GBM antibody nephritis and/or their antibodies.

Antibodies used in the remover include preferably either a polyclonal or monoclonal antibody and a monoclonal antibody is more preferable because it can be processed with semi-permanently constant activity in its property.

The removers of the present invention are specifically useful for some nephritis in need of urgent care such as anti GBM antibody nephritis etc.

Effect of the Invention

The present invention is useful for early detection or definite diagnosis of nephritis and for treatment of a nephritis patient or cancer patient.

EXAMPLE 1

[Isolation and purification of antigen] Isolate NC1 domain of type IV collagen (hereafter referred to as NC1) from bovine renal glomeruli as the raw material and purify it using column chromatography (J. Biol. Chem., 263, 10481-8).

Figure 1:
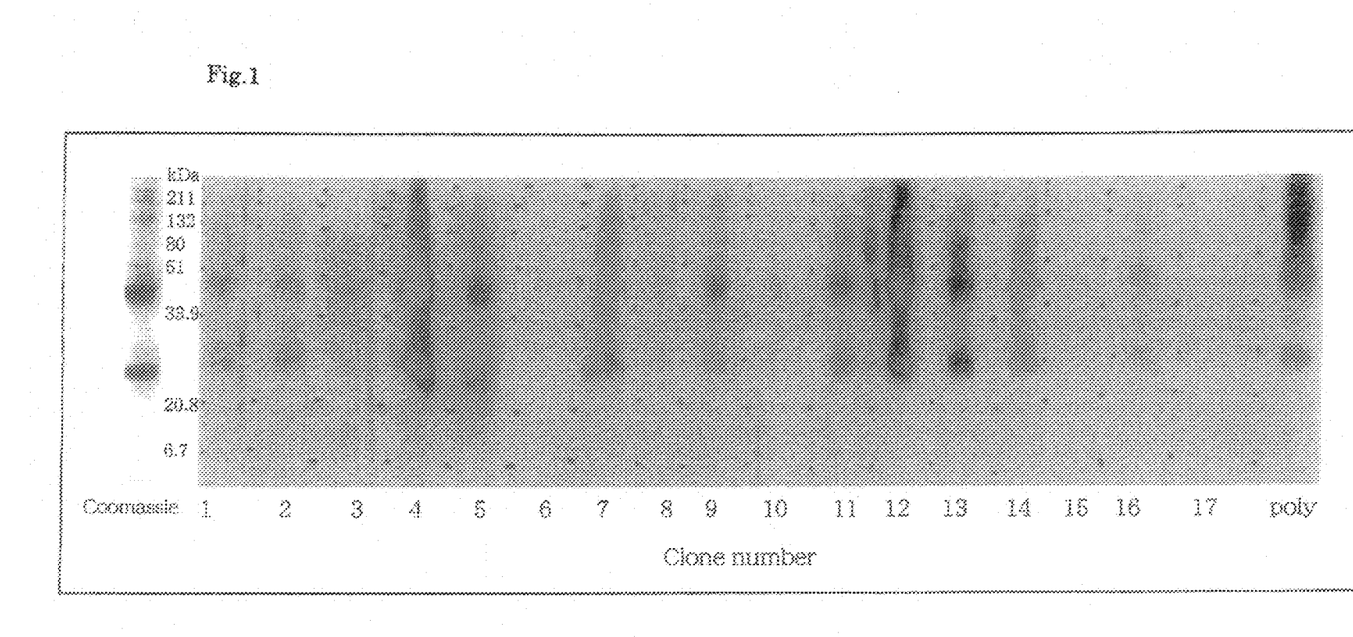
FIG. 1. Selection of antibody by Western blot method: Lane 17: Control; Poly.: Anti NC1 polyclonal antibody.
Figure 2:
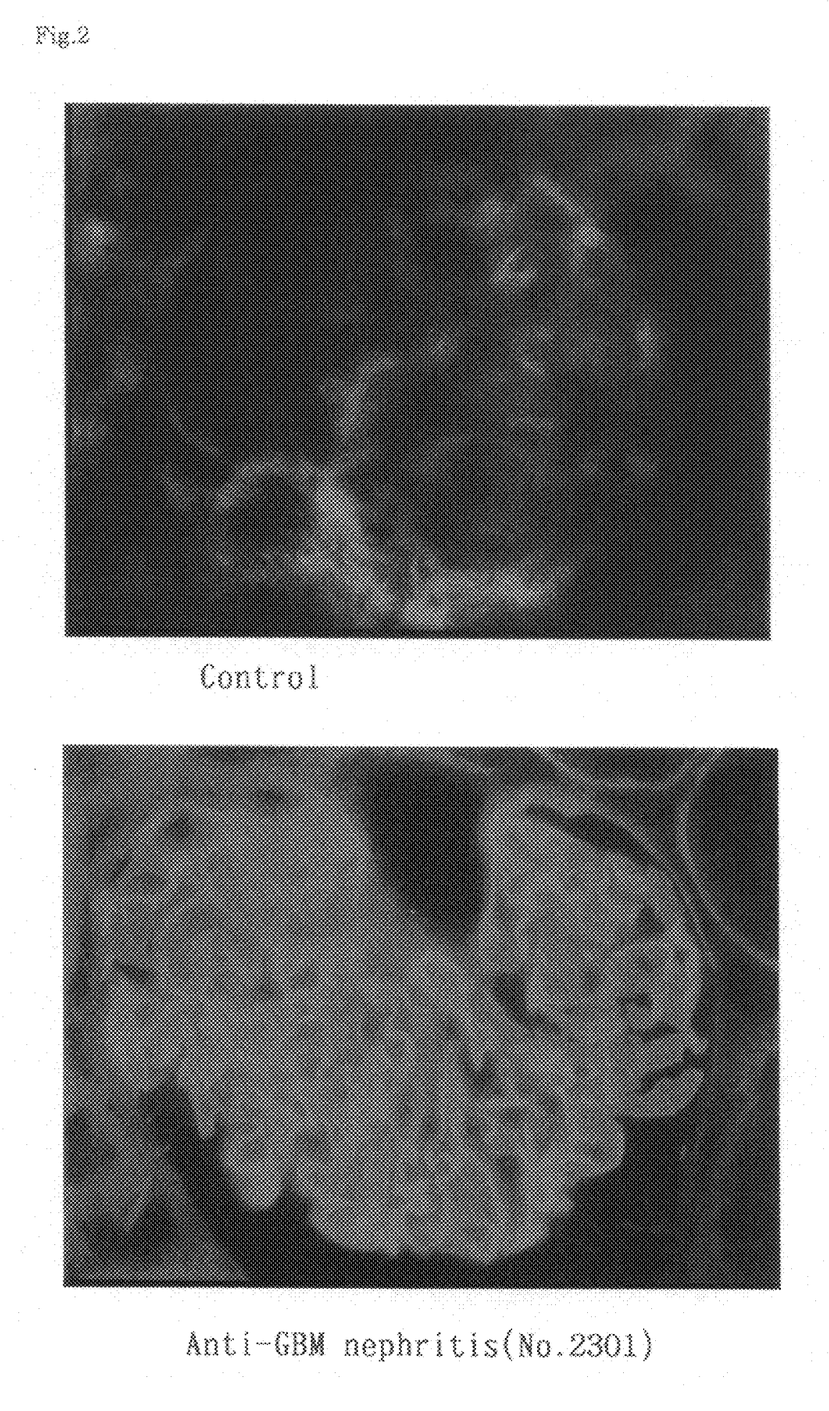
FIG. 2. Comparison of staining with anti NC1 monoclonal antibody between crab-eating macaque normal kidney and its nephritis model kidney (Indirect immunohistofluorescent stain).

[Preparation and selection of antibody] Prepare antibodies using the mouse (Monoclonal Antibody Experimental Manual. KODAN-Sha. 1987). For screening of cell fusion, select a lot of positive pores which possess high antibody titer using an ELISA method. After cellular proliferation of them in the mouse abdominal cavity, collect the ascitic liquid and select the antibody which reacts with both NC1 monomer and NC1 dimmer (FIG. 1). Then, perform an immunofluorescent staining using crab-eating macaque normal kidney and nephritis model kidney (anti GBM antibody nephritis) and select the antibody which reacts with the glomeruli of the crab-eating macaque anti GBM antibody nephritis but not with the crab-eating macaque normal kidney (Table 1, FIG. 2).

(The crab-eating macaque nephritis model of the present invention prepared hereupon, is different one in its administration site from the reported administration site previously. In this model of the present invention, the administration consists of 1 mg NC1 of the primary dorsal injection and 3 mg NC1 of the booster dorsal injection. Dorsal injection may not produce any difficulty in walking or in bipedal walking of the monkey and cause less infection compared to a plantar injection.)

[Experiment on NC1 Injection in Crab-Eating Macaque (Female, 3 Y.O.), 2 Animals in Each Group]

1) Administration site and method; The same doses of both NC1 and FCA were injected intracutaneously on the dorsal site of the animal.

2) Assay of anti NC1 antibody titer in the urine (diluted into 50-fold) (Assays were done before administration and 4 weeks after initial administration)

Changes of titer mean values of 2 animals

Single administration (4 mg) 0.018 ⇒0.087

Twice administrations (3 mg initial, 1 mg booster after 3 weeks)

0.029 ⇒0.256

Twice administrations (1 mg initial, 3 mg booster after 3 weeks)

0.006 ⇒1.037

3) Assay method; Urinal specimens were added onto a 96 wells micro-plate applied with NC1 (5 µg/ml) derived from bovine and incubated for 2 hours at room temperature. After washing, HRP labeled anti human IgG antibody was added and incubated for 1 hour at room temperature. After washing, a luminary substrate solution was initially added and after 10 minutes, a reaction stopper solution was secondarily added. Then, the absorbance at 450 nm of wave length (A450 nm) was immediately measured.

Figure 31:
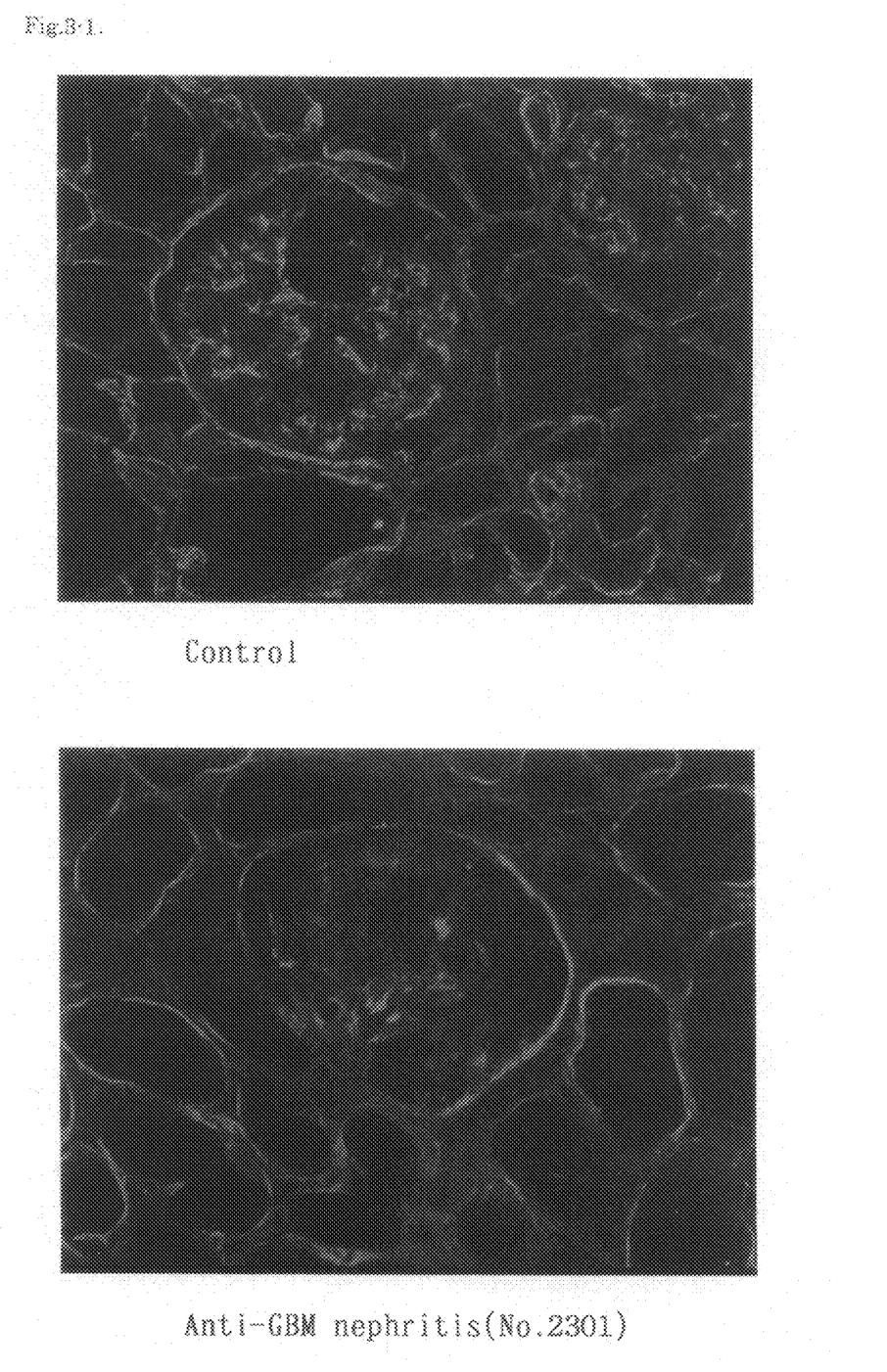
Figure 32:
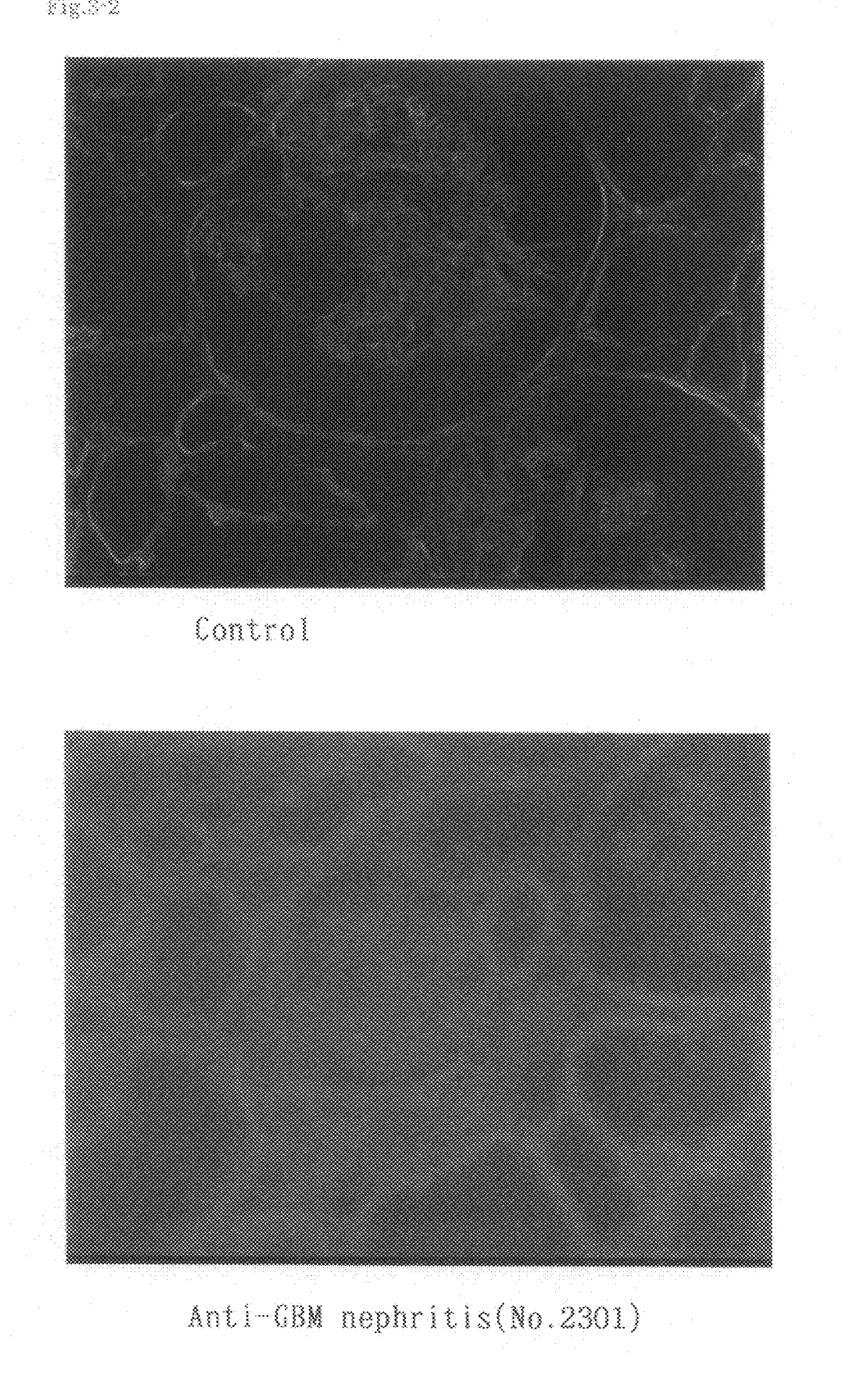

Furthermore, an anti human type IV collagen (antigen derived from placenta, pepsin treated) polyclonal antibody (derived from rabbit) and an anti NC1 polyclonal antibody (derived from rabbit) were prepared and their stainability was compared between in a monkey normal kidney and in a monkey nephritis model kidney using an indirect immunofluorescence method. While both the above kidneys were stained (FIGS. 3-1, FIGS. 3-2), the anti NC1 monoclonal antibody of the present invention is more stainable in the nephritis kidney rather than the in normal kidney.

Therefore, the anti NC1 monoclonal antibody of the present invention dedicates an useful staining reagent in order to detect nephritis.

In fact, the anti NC1 monoclonal antibody selected from the present invention can stain the kidney of human glomerulonephritis. For instance, the antibody can stain GBM and uriniferous tubule of the frozen kidney section from IgA nephropathy.

Figure 4:
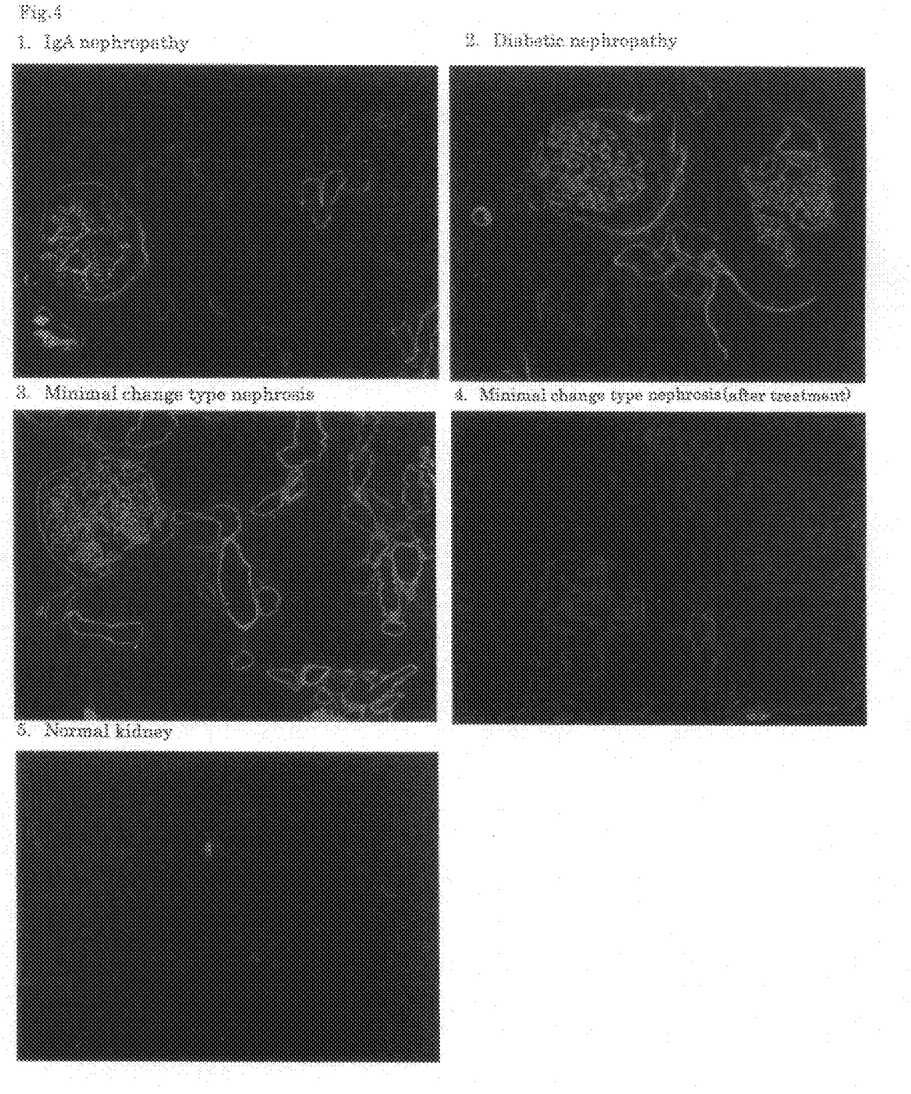
FIG. 4. Staining of kidneys of various human nephritis with anti NC1 monoclonal antibody (Indirect immunohistofluorescent stain).
Figure 5:
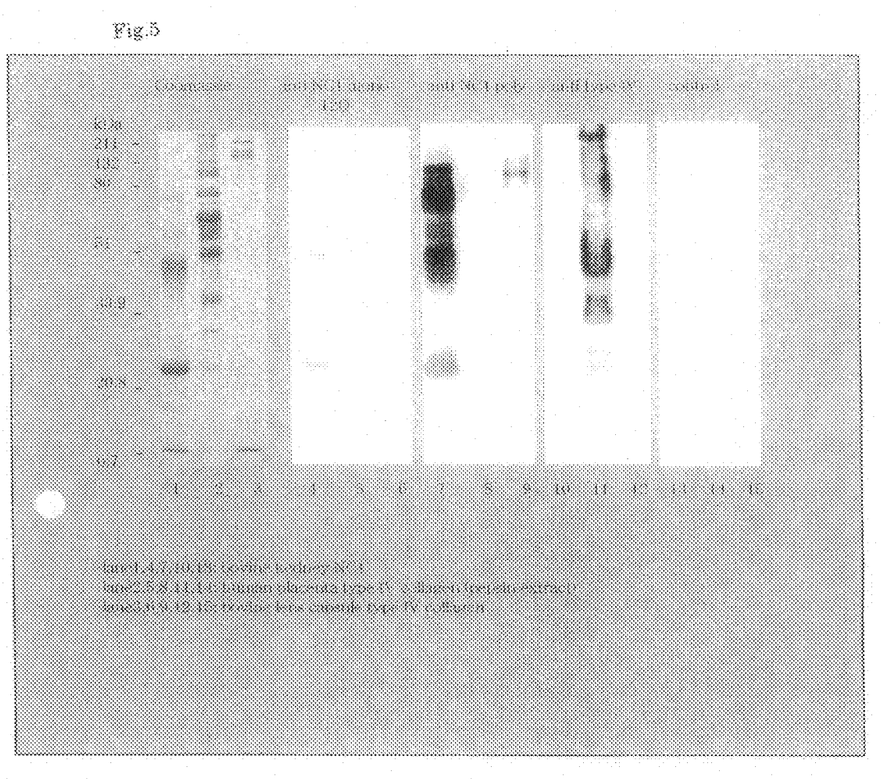
FIG. 5. Western blot method using both antigens of type IV collagen (derived human placenta, pepsin treated) and NC1 (derived bovine renal glomeruli, collagenase treated):
   anti NC1 mono 12D: anti NC1 monoclonal antibody;
   anti NC1 poly: anti NC1 polyclonal antibody;
   anti type IV: anti human type IV collagen polyclonal antibody;
   control: no addition of the primary antibody

The antibody of the present invention can stain kidneys in various types of human nephritis not only in IgA nephropathy but also in renal GBM. The antibody can more specifically stain glomeruli, uriniferous tubule, Bowman's capsule etc. in a minimal-change type primary nephrosis or a diabetic nephropathy. However, it does not stain kidneys which include those of a recovered minimal-change type nephrosis or normal kidney (FIG. 4). Furthermore, in order to confirm the specificity of this antibody, when its immunological response was examined by the Western blot method using type IV collagen (derived from human placenta, pepsin treated) and NC1 (derived from bovine renal glomeruli, collagenase treated) as antigens, the antibody responded to NC1 but did not respond to type IV collagen (FIG. 5). The anti NC1 monoclonal antibody of the present invention can be applicable either to an ELISA method, Western blot method or to immunofluorescent stain method.

EXAMPLE 2

Anti NC1 Antibody Remover and/or NC1 Remover

NC1 in sera can only be removed by dialysis of the blood through an affinity column prepared with an anti NC1 antibody. The anti NC1 antibody in sera can only be removed by dialysis of the blood through an affinity column prepared with NC1. After these treatments, the blood from which both antibody and antigen are removed will be recycled into the internal circulation of the body. In accordance with this principle, the blood equivalent to 4 ml of serum was collected from a nephritis model of crab-eating macaque (female, approx. 3 y.o.) and dialyzed through two kinds of affinity columns described above and then, recycled into the internal blood circulation of the animal and this procedure was subsequently repeated 3 times. When the both antibody titers in urine before and after treatment were assayed, the antibody titer after treatment decreased into less than half compared to that before treatment.

EXAMPLE 3

Type IV Collagen Assay Kit Prepared with Anti Type IV Collagen Antibody Made from Type IV Collagen Antigen Derived from Kidney It is well known that type IV collagen has chains from a 1 to a 6. Constitution of α-chains may differ upon the kinds of sourcing organ. A Type IV collagen derived from placenta possesses mainly α 1- and α 2-chains. On the contrary, a type IV collagen of kidney origin possesses α 3- and α 4-chains abundantly compared to the placenta origin. In order to obtain the type IV collagen derived from a kidney of the present invention, the following procedures can be done:

extract the collagen from bovine renal GBM using an usual pepsin-degradation method; and then, remove NC1 fine particles, which may be contaminated in this process, using anti NC1 affinity column prepared separately.

Consequently, pure type IV collagen derived from a kidney can be obtained through this process. At the same time, the antibody with specifically high titer can be obtained by making the type IV collagen to an antigen.

Measurement of Antibody Titer; the Following Procedures can be Done

Coat the antigen with 1) Bovine renal glomeruli pepsin soluble type IV collagen and 2) human placental pepsin soluble type IV collagen onto a 96 wells plate;

add 100 µl of specimen;

after incubation for 2 hours at room temperature, add HRP labeled antibody incubate them for one hour at room temperature;

add TMB solution and incubate them for 10 minutes at room temperature;

stop the reaction by 1N sulfuric acid stopper solution; and measure immediately the absorbance at 450 nm of wave length.

Specimens and Assay Results;
   Specimen/Anti human placental type IV collagen monoclonal antibody (Immune animal/mouse, 3 kinds; 1A, 1B, 1E);
      1) All minus (background deleted, the same bellow)
      2) 1A/1.826, 1B/2.188, 1E/2.222
   Specimen/Anti human placental type IV collagen polyclonal antibody (Immune animal/rabbit, YOK0203);
      1) 2.391
      2) 2.231
   Specimen/Marketed anti human placental type IV monoclonal antibody (Immune animal/mouse, F59)
      1) 0.047
      2) 2.135
   Specimen/Marketed anti human placental type IV polyclonal antibody (Immune animal/goat, GOAT);
      1) 0.450
      2) 2.037
   Only antibody YOKO responded to both bovine renal GBM pepsin soluble type IV collage and human placental pepsin soluble type IV collagen but other antibodies responded to only one of these type IV collagens.
Conclusion;
   For the measurement of renal type IV collagen, the reagent prepared with the antibody against renal type IV collagen antigen (ELISA kit etc.) is preferable.
   Further, the renal type IV collagen antigen is preferable to use in assaying anti type IV collagen antibody for evaluation of renal function.

EXAMPLE 4

Assay of Anti NC1 Antibody in IgA Nephropathy Model Higa Mouse

3 HIGA mice (female, 4 week aged) were purchased and bred for measurement. Test specimens were obtained from one sampling for blood specimen and several samplings per day for urine totalized specimen. The serum sample was diluted into 200-fold and the urine sample into 4-fold for measurement. An ELISA method was used for assay.
   Both IgA antibody and IgG antibody were detected in the sera of all animals aged 6 weeks or more.
   IgA antibody was detected in the urine of the animals aged 15 weeks and IgG antibody was detected in the urine of the animals aged 18 weeks.

BRIEF DESCRIPTION OF THE DRAWINGS

The patent or application file contains at least one drawing/photographs executed in color. Copies of this patent or application publication with color drawing(s)/photograph(s) will be provided by the Office upon request and payment of the necessary fee.

FIGS. 3-1. Comparison of staining with anti human type IV collagen (derived from placenta) polyclonal antibody (derived rabbit) between crab-eating macaque normal kidney and its nephritis model kidney (Indirect immunohistofluorescent stain).

FIGS. 3-2. Comparison of staining with anti NC1 polyclonal antibody (derived from rabbit) between crab-eating macaque normal kidney and its nephritis model kidney (Indirect immunohistofluorescent stain).

TABLE 1

Staining Procedure

Table 1.
Materials;
   Frozen renal tissues of crab-eating macaque anti GBM antibody nephritis model and normal one. (Embed into OCT compound, freeze rapidly using dry ice-acetone or liquid nitrogen, preserve at −80° C.).
Antibody;
   Primary antibody: Anti NC1 monoclonal antibody (derived from mouse);
   Secondary antibody: FITC labeled anti mouse antibody (derived from rabbit)
   (DAKO Inc., Code No. F0232, Lot. 045).
Procedure;
   1) Prepare frozen slice pieces using Cryostatt
   2) After drying, fix them for 5 minutes with acetone
   3) Wash with phosphoric acid buffer solution (PBS, pH 7.4)
   4) Incubate for 2 hours at room temperature with the primary antibody (diluted into 500-fold solution)
   5) Wash with PBS
   6) Incubate for 1 hour at room temperature with the secondary antibody (diluted into 50-fold solution)
   7) Wash with PBS
   8) Mount with glycerol

The invention claimed is:

1. A method of identifying presence of nephritis in a mammal at an early stage before formation of glomerular crescent or deposition of immunoglobulins, comprising:
   obtaining a biological sample of frozen kidney tissue from the mammal;
   exposing the sample to anti-noncollagenous domain of type IV collagen (NC1) monoclonal antibody, wherein said antibody exhibits substantially more binding to glomeruli of macaques in which nephritis has been induced by anti-glomerular basement membrane (GBM) antibody than to glomeruli of normal macaques; and
   identifying binding of the antibody to antigen present in the sample, wherein significant binding indicates presence of nephritis in the mammal.

2. The method according to claim 1, wherein identifying binding of the antibody comprises an immune reaction assay.

3. The method according to claim 1, wherein identifying binding of the antibody comprises an enzyme-linked immunoassay.

4. The method according to claim 1, wherein identifying binding of the antibody comprises an assay selected from the group consisting of an avidin-biotin (AB) method, a radioimmunoassay (MA) method, and an immunoluminescence method.

5. The method according to claim 1, wherein identifying binding of the antibody comprises immunofluorescent staining.

6. The method according to claim 1, wherein the presence of nephritis is identified before granular deposition of IgA into renal glomerular basement membrane (GBM) of the mammal.

7. The method according to claim 1, wherein the mammal has symptoms of anti glomerular basement membrane (GBM) antibody nephritis.

8. A method of identifying presence of nephritis in a mammal, comprising:
   obtaining a biological sample from the mammal, wherein said sample is a frozen kidney tissue of the mammal;
   exposing the sample to anti-noncollagenous domain of type IV collagen (NC1) monoclonal antibody, wherein said antibody is configured to have a substantially higher affinity to a frozen kidney tissue obtained from a mammal under condition of nephritis than a frozen kidney tissue obtained from a mammal under a normal condition;
   identifying binding of the antibody to antigen present in the sample, wherein significant binding indicates presence of nephritis in the mammal,
   wherein said method is configured to identify presence of nephritis at an early stage, said stage being before formation of glomerular crescent.

9. The method according to claim 8, wherein the mammal has symptoms of anti glomerular basement membrane (GBM) antibody nephritis.

10. A method of identifying presence of nephritis in a mammal, comprising:
    obtaining a biological sample from the mammal, wherein said sample is a frozen kidney tissue of the mammal;
    exposing the sample to anti-noncollagenous domain of type IV collagen (NC1) monoclonal antibody; and
    identifying binding of the antibody to antigen present in the sample, wherein significant binding indicates presence of nephritis in the mammal,
    wherein said method is configured to identify presence of nephritis at an early stage, said stage being before formation of glomerular crescent; and
    wherein said antibody is selected via a process comprising:
    obtaining a biological sample that is sectioned from frozen kidney tissue of a mammal; and
    selecting an anti-noncollagenous domain of type IV collagen (NC1) monoclonal antibody that binds to a frozen kidney tissue obtained from a mammal under condition of nephritis but not to a frozen kidney tissue obtained from a mammal under a normal condition.

11. The method according to claim 10, wherein the mammal has symptoms of anti glomerular basement membrane (GBM) antibody nephritis.

* * * * *

UNITED STATES PATENT AND TRADEMARK OFFICE
CERTIFICATE OF CORRECTION

PATENT NO. : 8,039,226 B2
APPLICATION NO. : 10/589420
DATED : October 18, 2011
INVENTOR(S) : Tsukao Yokoyama and Toshiyuki Imasawa It is certified that error appears in the above-identified patent and that said Letters Patent is hereby corrected as shown below:

At column 1, line 50, Change "aspired" to --aspired.--.

At column 5, line 43, Change "stainability" to --sustainability--.

At column 7, line 12, Change "F59)" to --F59);--.

At column 8, line 14, (Approx.), Change "antibody" to --antibody.--.

At column 8, line 30, Change "rabbit)" to --rabbit);--.

At column 8, line 33, Change "Cryostatt" to --Cryostat--.

Signed and Sealed this
Twenty-sixth Day of June, 2012

David J. Kappos
*Director of the United States Patent and Trademark Office*